US00PP10055P

United States Patent [19]

Challet

[11] Patent Number: Plant 10,055

[45] Date of Patent: Oct. 7, 1997

[54] CHRYSANTHEMUM PLANT NAMED 'CHABURGA'

[75] Inventor: Jean Pierre Challet, Nuaille, France

[73] Assignee: Selection New Plant Sarl, Le Luc, France

[21] Appl. No.: 710,151

[22] Filed: Sep. 12, 1996

[51] Int. Cl.[6] ..... A01H 5/00

[52] U.S. Cl. ..... Plt./77

[58] Field of Search ..... Plt./77

*Primary Examiner*—Howard J. Locker

*Attorney, Agent, or Firm*—Burns, Doane, Swecker & Mathis, L.L.P.

[57] ABSTRACT

A new and distinct Chrysanthemum cultivar named 'Chaburga' is provided. The new cultivar was the result of a controlled breeding program. Attractive very large double incurved blossoms of the pompon type are formed that are pure white on the inner and outer surfaces. The blossom incurving is particularly pronounced at the tips of the ray florets. The blossoms are long lasting and keep their form for approximately three weeks. The response period of the flowers is approximately ten weeks. Recurrent profuse flower production throughout the year is made possible. The plant possesses strong stems, forms large dark green glossy leaves, and commonly assumes a height of approximately 35 to 40 cm. The blossom coloration contrasts nicely with the dark green foliage. The new cultivar is particularly suited for use in the production of a decorative pot Chrysanthemum that grows well single stem or disbudded. No growth regulator is necessary to achieve the relatively short plant height.

1 Drawing Sheet

SUMMARY OF THE INVENTION

The present invention comprises a new and distinct cultivar of Chrysanthemum, botanically known as *Dendranthema grandiflora*, and hereinafter is referred to by the name 'Chaburga'.

The new cultivar is the product of a planned breeding program which had as its objective the creation of a new Chrysanthemum cultivar that is intended primarily for pot mum production.

The breeding program which resulted in the production of the new cultivar of the present invention was carried out in a controlled environment during November 1989 at Nuaille, Trementines, France. The female parent (i.e., the seed parent) was a plant designated '88192-2' (non-patented in the United States and has never been commercialized) having large white flowers, poor foliage, a response time of twelve weeks, and a tall plant height, and the male parent (i.e., the pollen parent) was a plant designated '8419-8' (non-patented in the United States and never has been commercialized) having a very nice glossy foliage. The parentage of the new cultivar can be summarized as follows:

'88192-2'×'8419-8'.

The seeds resulting from the above pollination were sown and many small plantlets were obtained which were physically and biologically different from each other. Selective study resulted in the identification of a single plant of the new variety.

It was found that the new cultivar of the present invention:

(a) exhibits attractive large double incurved pompon blossoms that are pure white on the inner and outer surfaces,
(b) exhibits a flower response period of approximately ten weeks,
(c) forms attractive dark green glossy foliage,
(d) achieves a short plant height, and
(e) is particularly suited for pot mum production on a recurrent basis throughout the year.

The new cultivar is intended primarily as a decorative pot Chrysanthemum for growing indoors. However, it also can be grown for cut flower production in those instances where stems of approximately 40 cm. or less are acceptable. Also, the new cultivar can be grown outdoors at temperatures above freezing.

In the absence of debudding approximately 6 to 10 blossoms commonly form per stem. The new cultivar can be grown single stem or disbudded. An increased number of branches readily can be induced by pinching. The pinching of a cutting commonly produces approximately 3 or 4 stems per cutting. No growth regulator is required to produce the short plant height; however, a growth regulator optionally can be utilized.

The new cultivar can be considered to be an October-flowering greenhouse variety with the natural flowering season commonly occuring in weeks 42 and 43 of the year. Attractive blossoms can be produced on a recurrent basis throughout the year with the indicated ten week response period. The blossoms are long lasting and commonly can be maintained on the plant for approximately three weeks.

Asexual reproduction of the new cultivar by cuttings initially taken during 1990, as performed in Nuaille, Trementines, France, in a controlled environment has demonstrated that the characteristics of the new cultivar as herein described are firmly fixed and are retained through successive generations of asexual propagation.

'Chaburga' has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the 'May Shoesmith' cultivar (non-patented in the United States), the 'Chaburga' cultivar is found to exhibit a faster response period of approximately 10 weeks vs. 12 weeks, and a shorter plant height.

When the new cultivar of the present invention is compared to the 'Charibo' cultivar (U.S. Plant Pat. No. 9,478), the new 'Chaburga' cultivar is found to exhibit a shorter plant height, a whiter flower coloration (i.e., the immature ray florets are pure white vs. cream to Yellow-Green Group 145C), and foliage of better quality.

The new 'Chaburga' cultivar is being marketed under the OBOE trademark.

BRIEF DESCRIPTION OF THE PHOTOGRAPH

The accompanying photograph was prepared during March, 1996, and shows as nearly true as it is reasonably possible to make the same in a color illustration of this character, typical plants and plant parts of the new cultivar of the present invention. The plants were twelve weeks of age and were grown at Nuaille, Trementines, France, under standard greenhouse conditions which approximate those commonly utilized for the production of decorative pot mums. The plants had been disbudded in order to encourage the formation of one large bloom per stem.

DETAILED DESCRIPTION

Figures 1, 2, 3, 4, 5, 6, 7, 8, 9, 10, 11, 12, 13:
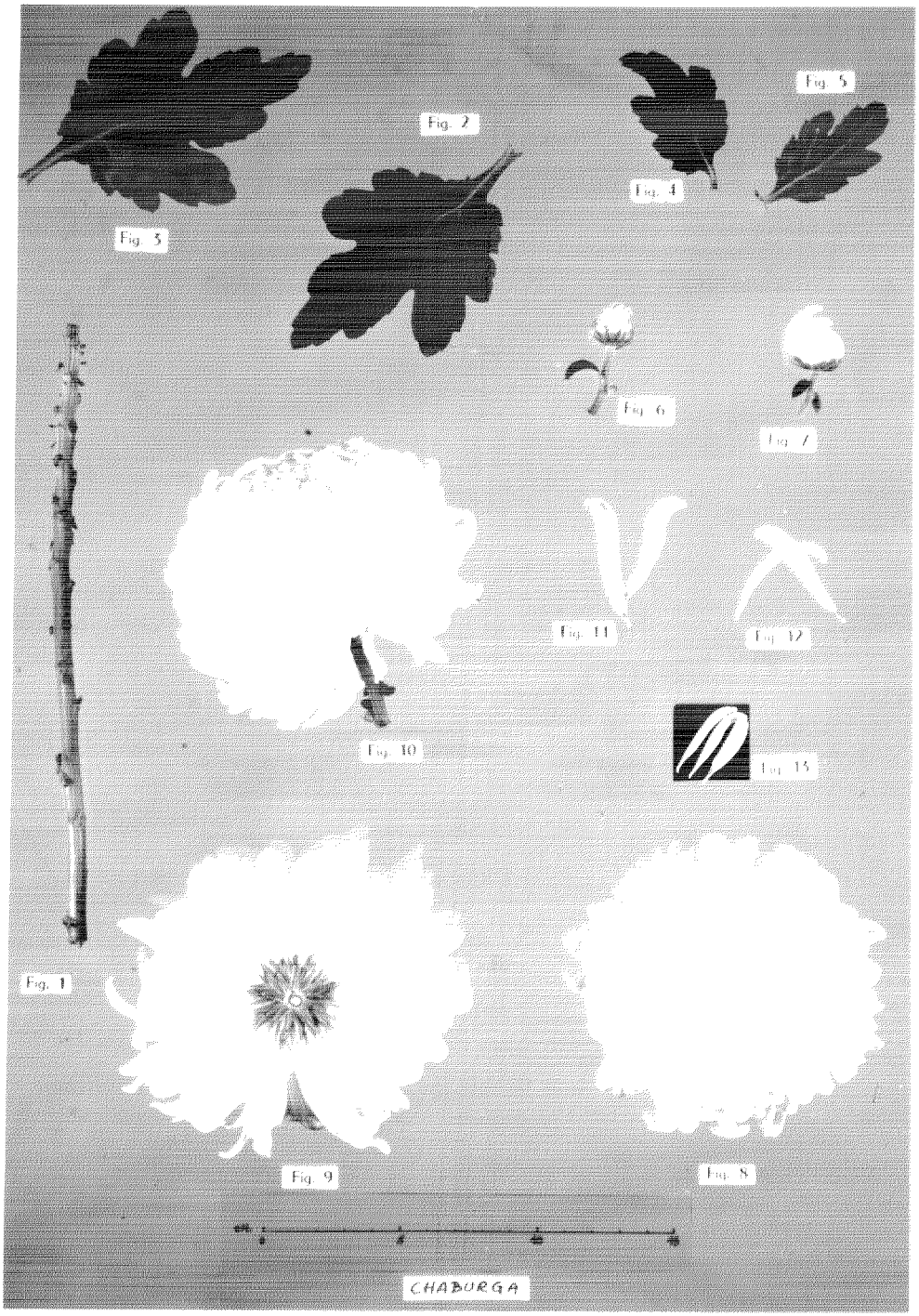
FIG. 1 illustrates a typical stem.
FIG. 2 illustrates the upper surface of a typical leaf from the lower part of the stem.
FIG. 3 illustrates the under surface of a typical leaf from the lower part of the stem.
FIG. 4 illustrates the upper surface of a typical leaf from the upper part of the stem.
FIG. 5 illustrates the under surface of a typical leaf from the upper part of the stem.
FIG. 6 illustrates the side view of an unopened bud.
FIG. 7 illustrates the side view of a typical flower as opening begins.
FIG. 8 illustrates an obverse view of a fully opened flower.
FIG. 9 illustrates a reverse view of a typical fully opened flower.
FIG. 10 illustrates the side view of a typical fully opened flower.
FIG. 11 illustrates the top view of two typical outer ray-florets.
FIG. 12 illustrates the under view of two typical outer ray-florets.
FIG. 13 illustrates the left to right, side, and top views of three typical inner ray-florets.

The chart used in the identification of colors described hereafter is The R.H.S. Colour Chart of The Royal Horticultural Society, London, England. In some instances more common color terms are provided and are to be accorded their usual dictionary significance. The plants described were grown at Nuaille, Trementines, France, in 20 cm. pots, three plants to a pot, were rooted in early June, and were stopped in mid-July. All primary laterals were retained. Disbudding was carried out to leave the terminal flower heads, the plants were grown outdoors until late September, and then were grown in greenhouses provided at a minimum of 15.5° C. These conditions were deemed to approximate those commonly utilized for the production of decorative pot mums.

Classification:

*Botanical.*—*Dendranthema grandiflora*, cv. 'Chaburga'.

*Commerical.*—Decorative pot mum.

Inflorescence

A. Capitulum:

*Form.*—Large, double, incurved, and commonly exhibiting a perfect configuration. The incurving is particularly strong at the tips.

*Type.*—Pompon.

*Diameter across face.*—Approximately 12 to 14 cm. on average when fully expanded.

B. Corolla of ray and disc florets:

*Color of bud.*—Pure white (as illustrated).

*Disc florets.*—Tubular, absent or very few in number, typically less than 25, scattered among the ray florets, and very difficult to observe.

*General tonality.*—White.

*Color ray florets.*—White Group 155D but somewhat whiter and brighter.

*Configuration ray petals.*—The longitudinal axis of most petals is very strongly incurved along the distal half. The longitudinal axis of the outer rows is strongly to very strongly incurved at the tip. The length of the corolla tube of the ray florets is very short. The ray florets have a cross-section which is strongly concave, and possesses one keel, so that the ray florets often are more or less V-shaped in cross-section. The thickness of the ray florets is medium and their surfaces are textured. The tips of the ray florets commonly are pointed as well as hooked. The ray florets commonly are approximately 52 mm. in length and approximately 10 mm. in width on average.

C. Reproductive organs:

*Androecium.*—Generally present with disc florets and absent in the ray florets.

*Gynoecium.*—Generally present with most disc florets and with most ray florets.

*Pollen.*—Formed in a sparse quantity and golden-yellow in coloration.

*Fragrance.*—Typical of Chrysanthemum.

Plant

A. General appearance:

*Height.*—Short, and approximately 35 to 40 cm. in height on average.

B. Foliage:

*Color.*—Near Yellow-Green Group 147A and slightly more green.

*Configuration.*—Lobed (as illustrated).

*Texture.*—Fleshy.

*Serration.*—Fine to medium.

*Length of lower lobe.*—Short, but usually absent, and generally possess three-lobed leaves.

*Shape of base.*—Rounded.

*Claw in base of sinus between lateral lobes.*—Absent.

*Margins of sinus between lateral lobes.*—Converging.

*Apex.*—Mucronate.

*Stems.*—Strong, angular in cross section, near Yellow-Green Group 146B in coloration, and commonly with anthrocyanin coloration at the nodes and ocassionally at the base.

I claim:

1. A new and distinct cultivar of Chrysanthemum plant named 'Chaburga', substantially as herein shown and described, which:

(a) exhibits attractive large double incurved pompon blossoms that are pure white on the inner and outer surfaces,
(b) exhibits a flower response period of approximately ten weeks,
(c) forms attractive dark green glossy foliage,
(d) achieves a short plant height, and
(e) is particularly suited for pot mum production on a recurrent basis throughout the year.

* * * * *

CHABURGA